United States Patent [19]

Yokoo et al.

[11] Patent Number: 4,842,640

[45] Date of Patent: Jun. 27, 1989

[54] OXADIAZOLONE DERIVATIVE, PRODUCTION PROCESS THEREOF, AND HERBICIDE CONTAINING SAME

[75] Inventors: Hidejiro Yokoo, Fukushima; Toshishiro Maruyama, Ibaraki; Yasuhide Toshima, Kawasaki; Yasuo Kobori, Saitama, all of Japan

[73] Assignee: Rhone-Poulenc Agrochimie, Lyons, France

[21] Appl. No.: 128,602

[22] Filed: Dec. 4, 1987

[30] Foreign Application Priority Data

Dec. 16, 1986 [JP]   Japan ................................ 61-297457

[51] Int. Cl.$^4$ .................... C07D 271/10; A01N 43/82

[52] U.S. Cl. ......................................... 71/92; 548/144
[58] Field of Search ............................ 548/144; 71/92

[56] References Cited

U.S. PATENT DOCUMENTS 3,818,026  6/1974  Boesch ................................ 548/144

Primary Examiner—Robert Gerstl
Attorney, Agent, or Firm—Burns, Doane, Swecker & Mathis

[57] ABSTRACT

A novel compound, 5-t-butyl-3-(4-chloro-2-fluoro-5-propargyloxy-phenyl)-1,3,4-oxadiazol-2-one, useful as an active ingredient of a herbicide, and a production process thereof are disclosed.

6 Claims, No Drawings

OXADIAZOLONE DERIVATIVE, PRODUCTION PROCESS THEREOF, AND HERBICIDE CONTAINING SAME

BACKGROUND OF THE INVENTION

1. Field of the Invention

The present invention relates to a novel compound, 5-t-butyl-3-(4-chloro-2-fluoro-5-propargyloxyphenyl)-1,3,4-oxadiazol-2-one, a production process thereof, and a herbicide containing the same as an active ingredient.

2. Description of the Related Art

The above-mentioned compound is novel and has a superior herbicidal activity never before described in literature or disclosed in a patent. Although compounds having a similar structure are known. For example, a compound having the following formula is disclosed in U.S. Pat. No. 3385862.

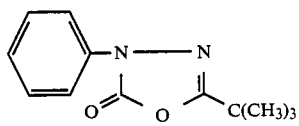

wherein the phenyl ring is not substituted or is substituted with one to four substituent groups selected from halogen atoms and alkyl and alkoxy groups having 1 to 4 carbon atoms.

Also, a compound having the following formula is disclosed in U.S. Pat. No. 3818026.

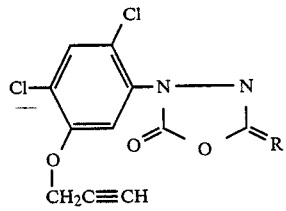

wherein R denotes a linear or branched $C_1$–$C_4$ alkyl group or $C_2$–$C_4$ alkenyl group.

The compounds disclosed in the prior art include those having a good herbicidal activity, and some of those compounds have been put to practical use. Nowadays, herbicides must have a higher activity, to ensure safety and for reasons of economy, and thus the appearance of a new generation of herbicides is expected. Accordingly, the above-mentioned compounds disclosed in the prior art do not necessarily have a satisfactory herbicidal activity, and there is an increasing demand for a compound having a higher activity.

SUMMARY OF THE INVENTION

In an attempt to develop a compound having a high herbicidal activity, the present inventors synthesized and tested a large number of compounds to determine if such compounds are useful as a herbicide. As a result, it was unexpectedly found that the above-mentioned compound has a high herbicidal activity which is not anticipated from prior art, and the present invention was completed on the bsais of this finding.

Accordingly, it is an object of the present invention to provide a compound 5-t-butyl-3-(4-chloro-2-fluoro-5-propargyloxy-phenyl)-1,3,4-oxadiazol-2-one represented by the following structural formula, and a herbicide containing that compound as an active ingredient.

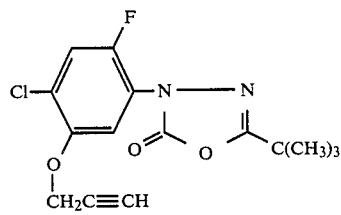

The compound according to the invention represented by the above structural formula, in which the benzene ring is substituted by a fluorine atom, is not only novel but also the herbicidal activity thereof is unknown. The present inventors investigated ways of increasing the herbicidal activity by introducing a fluorine atom into the benzene ring, and as a result, unexpectedly found that the compound represented by the following formula exhibits a specifically high herbicidal activity.

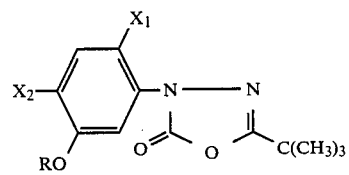

wherein $X_1$ is a fluorine atom, $X_2$ is a chlorine atom, and R is a $C_1$–$C_6$ alkyl group or a $C_3$–$C_4$ alkenyl group or alkynyl group. That is, this compound has a weak or almost no herbicidal effect when $X_1=F$, $X_2=H$; $X_1=Cl$, $X_2=F$; or $X_1=H$, $X_2=F$, and the above extremely high activity was obtained only when $X_1=F$ and $X_2=Cl$. It was also found that the highest herbicidal effect was obtained when R is a propargyl group represented by —$CH_2C$—CH. This compound was found to have a much higher herbicidal activity than that of the compound designated as (D) in the above-mentioned prior art, the formula of which is shown below.

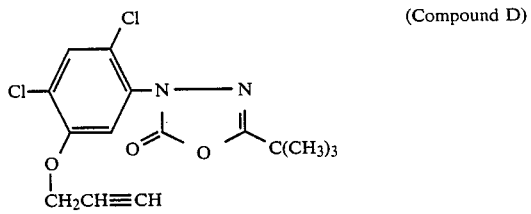

(Compound D)

This is a surprising effect which could not be predicted from the above-mentioned prior art, and thus the present invention makes it possible to control noxious weeds at a low dosage and provides an extremely economical way of weeding. In addition, the compound of the invention is extremely safe for warm-blooded animals.

The compound of the invention can be produced through the following reactions.

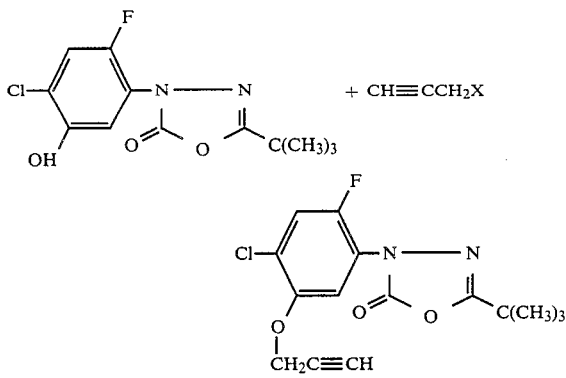

wherein X denotes a chlorine atom or bromine atom. In other words, the compound of the invention can be produced by reacting 5-t-butyl-3-(4-chloro-2-fluoro-5-hydroxy-phenyl)-1,3,4-oxadiazol-2-one with propargyl chloride or propargyl bromide.

The reaction can be carried out in an aprotic solvent such as acetonitrile, DMF, DMSO, acetone, methyl ethyl ketone, chloroform, and methylene chloride, or a protic solvent such as methanol, ethanol, propanol, isopropanol, and butanol, or a mixed solvent thereof. Preferably the reaction is carried out in the presence of a basic substance. Examples of the basic substance include alkali metal carbonates such as potassium carbonate, sodium carbonate, and sodium bicarbonate; alkali metal hydroxides such as sodium hydroxide and potassium hydroxide; and alkali metal alkoxide such as sodium methoxide and sodium ethoxide. The reaction temperature is 10° to 150° C., preferably 40° to 110° C.

The starting material in the above reaction, i.e., 5-t-butyl-3-(4-chloro-2-fluoro-5-hydroxyphenyl)-1,3,4-oxadiazol-2-one can be obtained by reacting 5-t-butyl-3-(4-chloro-2-fluoro-5-isopropoxyphenyl)-1,3,4-oxadiazol-2-one with aluminum chloride. This 5-t-butyl-3-(4-chloro-2-fluoro-5-isopropoxy-phenyl)-1,3,4-oxadiazol-2-one can be obtained by cyclizing a phenylhydrazine derivative represented by the formula below with phosgene.

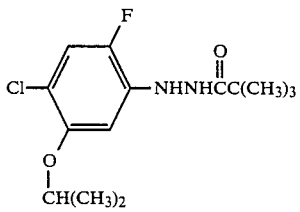

The phenylhydrazine derivative can be obtained by acylating phenylhydrozine represented by the formula below with pivalic acid chloride.

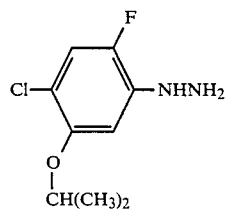

The phenylhydrazine can be obtained by the following process. First, 2-chloro-4-fluoro-5-nitrophenol (which is disclosed by, for example, Japanese Examined Patent Application (Kokoku) No. 10661/1974) alkylated with isopropyl bromide or isopropyl chloride in acetonitrile in the presence of potassium carbonate to give 4-chloro-2-fluoro-5-isopropoxy-nitrobenzene. The nitro group in this compound is reduced to an amino group and the amino group is diazotized. The thus produced compound is finally reduced with freshly produced sodium bisulfate, as disclosed in the Journal of Organic Chemistry 30, 3946 (1965), or stannous chloride, as disclosed in the Journal of the Americal Chemical Society 70, 1381 (1948).

The compound of the invention exhibits a very strong herbicidal activity when used by foliage application or soil application in upland fields; is highly effective against such weeds as Mehishiba (Digitaria ciliaris), Inubiyu (*Echinochloa crus-galli*), Shiroza (*Chenopodium album*), Nagabagishigishi (*Rumex crispus*), Aobiyu (Amaranthus viridis), Marubaasagao (*Ipomoea coccinea*), Himejion (*Erigeron annuus*), Inugarashi (*Rorippa indica*), Enokorogusa (*Setaria viridis*), and Oonamomi (*Xanthium canadense*); and does not cause chemical injury to useful crop plants such as corn, wheat, upland rice, soybean, cotton, and sunflower.

In addition, when applied to wet rice fields, the compound of the invention is also effective against annual weeds such as Tainubie (*Echinochloa oryzicola*), Himemisohagi (*Ammannia multiflora*), and Konagi (*Monochoria vaginalis*) and perennial weeds such as Hotarui (*Scirpus juncoides*), Urikawa (*Sagittaria pygmaea*), and Mizugayatsuri (*Cyperus serotinus*), but does not cause chemical injury to the rice.

The compound of the invention also can be an active ingredient of herbicides for lawns and non-crop land.

Where the compound of the invention is used as an active ingredient of herbicides, it can be formulated as granules, wettable powder, an emulsion, or a liquid, etc. by mixing with adjuvants such as solid carrier, liquid carrier, and surface active agent. The content of the compound of the invention as an active ingredient ranges from 0.05 to 80%, depending on the type of formulation.

Examples of the solid carrier include clay, kaolin clay, talc, diatomaceous earth, bentonite, acid clay, calcium carbonate, and vegetable powder. Examples of the liquid carrier include toluene, xylene, methylnaphthalene, butanol, isopropanol, ethylene glycol, cyclohexanone, methyl ethyl ketone, and animal and vegetable oils.

The compound of the invention also can be used in combination with not only other herbicides but also other agricultural insecticides and fungicides, plant growth regulators, and fertilizers.

The dosage as a herbicide varies according to the weeds, application time, application method, soil condition, etc., but ranges from 0.05 to 50 g per are, preferably 0.1 to 50 g per are.

EXAMPLES

The present invention will now be explained in further detail by showing Examples, Comparative Examples, and Reference Examples, but the scope of the present invention is not, of course, limited to these Examples. The compounds used for comparison are shown in Table 1, and those which are not publicly known are produced as described in Referential Example Nos. 1 to 3.

TABLE 1

| Compound designation | Chemical Formula | Remarks |
|---|---|---|
| A | [structure: 2-fluoro-5-(propargyloxy)phenyl-1,3,4-oxadiazol-2-one with t-butyl] | See Ref. Example 1 for manufacturing process and properties. |
| B | [structure: 4-fluoro-3-(propargyloxy)phenyl-1,3,4-oxadiazol-2-one with t-butyl] | See Ref. Example 2 for manufacturing process and properties. |
| C | [structure: 2-chloro-4-fluoro-5-(propargyloxy)phenyl-1,3,4-oxadiazol-2-one with t-butyl] | See Ref. Example 3 for manufacturing process and properties. |
| D | [structure: 2,4-dichloro-5-(propargyloxy)phenyl-1,3,4-oxadiazol-2-one with t-butyl] | Disclosed in U.S. Pat. No. 3818026 |
| E | [structure: 2,4-dichloro-5-(isopropoxy)phenyl-1,3,4-oxadiazol-2-one with t-butyl] | Commercial herbicide Oxadiazon |

Referential Example 1

(Process for producing Compound A)

A compound 5-t-butyl-3-(2-fluoro-5-isopropoxyphenyl)-1,3,4-oxadiazol-2-one was obtained in the form of crystal having a melting point of 67°–68.5° C., from p-fluorophenol as a starting material, in almost the same process as that used for the production of the compound according to the invention. The resultant compound was stirred in methylene chloride in the presence of anhydrous aluminum chloride to give 5-t-butyl-3-(2-fluoro-5-hydroxy-phenyl)-1,3,4-oxadiazol-2-one. This compound was alkylated with propargyl bromide to give 5-t-butyl-3-(2-fluoro-5-propargyloxyphenyl)-1,3,4-oxadiazol-2-one having a melting point of 80°–81° C. The structure was confirmed by NMR spectrum, mass spectrum, and IR spectrum.

Referential Example 2

(Process for producing Compound B)

The compound 5-t-butyl-3-(4-fluoro-3-isopropoxyphenyl)-1,3,4-oxadiazol-2-one (m.p. 72.5°–74° C.) was obtained as an intermediate from o-fluorophenol as a starting material, in almost the same process as that used for Referential Example 1. Subsequently this compound was made into the desired product 5-t-butyl-3-(4-fluoro-3-propargyloxyphenyl)-1,3,4-oxadiazol-2-one having a melting point of 87°–90° C. The structure was confirmed by NMR spectrum and IR spectrum.

Referential Example 3

(Process for producing Compound C)

The intermediate 5-t-butyl-3-(4-fluoro-3-isopropoxyphenyl)-1,3,4-oxadiazol-2-one obtained in Referential Example 2 was reacted with sulfuryl chloride in methylene chloride as a solvent, to give 5-t-butyl-3-(2-chloro-4-fluoro-5-isopropoxyphenyl)-1,3,4-oxadiazol-2-one having a melting point of 67°–69° C. Subsequently, this compound was made into the desired product 5-t-butyl-3-(2-chloro-4-fluoro-5-propargyloxyphenyl)-1,3,4-oxadiazo-1-2-one having a melting point of 114.5°–117° C. The structure was confirmed by NMR spectrum and IR spectrum.

Example 1

Reacted at 80° C. for 6 hours with stirring were 1.2 g of 5-t-butyl-3-(4-chloro-2-fluoro-5-hydroxyphenyl)-1,3,4-oxadiazol-2-one, 0.76 g of 3-bromopropyne, 40 ml of acetonitrile, and 0.3 g of potassium carbonate. After cooling, the reaction product was filtered and the filtrate was subjected to vacuum distillation to remove the solvent. To the residue was added 30 ml of methylene chloride, and the solution was washed with a 5% aqueous solution of sodium hydroxide and then with water. Upon removal of the solvent by distillation, 1.31 g of 5-t-butyl-3-(4-chloro-2-fluoro-5-propargyloxyphenyl)-1,3,4-oxadiazol-2-one was obtained. Upon recrystallization from n-hexane, a compound having a melting point of 72°–73° C. was obtained.

NMR (200 MHz, $CDCL_3$) δ ppm 2.60 (1H, t, J=2.44 Hz), 4.78 (2H, d, J=2.44 Hz), 7.25 (1H, d, J=6.35 Hz), 4.30 (1H, d, J=9.52 Hz)

IR (KBr tablet) $cm^{-1}$ 3277, 1772

Production of 5-t-butyl-3-(4-chloro-2-fluoro-5-hydroxyphenyl)-1,3,4-oxadiazol-2-one: 5 g of 5-t-butyl-3-(4-chloro-2-fluoro-5-isopropoxyphenyl)-1,3,4-oxadiazol-2-one was dissolved in methylene chloride, and to the solution was added 10 g of finely divided anhydrous aluminum chloride, followed by stirring at 25°–30° C. for 2 hours. Ice was added to the reaction mixture, the organic layer was washed with water, the solvent was distilled off, and 4.7 g of the desired product was obtained. A portion of the product was recrystallized from n-hexane to give a product having a melting point of 117°–119° C. Production of 5-t-butyl-3-(4-chloro-2-fluoro-5-isopropoxyphenyl)-1,3,4-oxadiazol-2-one: 8.5 g of 4-chloro-2-fluoro-5-isopropoxyphenyl-hydrazine was dissolved in 80 ml of toluene, and to the solution was added 19 ml of 10% aqueous solution of sodium hydroxide with thorough stirring. Then, 5.4 g of trimethylacetyl chloride was added dropwise over 5 minutes to the solution and stirring was continued for 3 hours at room temperature. The organic layer was separated and washed with a 5% aqueous solution of sodium hydroxide and then with water, the thus obtained organic layer was transferred to a flask, and gaseous phosgene was introduced into the flask at 40°–80° C. for 3 hours.

After cooling, the reaction liquid was washed with alkaline water and then with water, the solvent was distilled off, and 12 g of the desired product was obtained. Upon recrystallization from water-ethanol mixed solvent, a compound having a melting point of 83°–85.5° C. was obtained.

The compound of the invention produced as mentioned above was formulated into herbicides according to the formulations shown in the following Examples 2 to 6, in which "parts" means "parts by weight".

Example 2

A wettable powder was produced by crushing and mixing 50 parts of the compound of the invention, 2 parts of sodium lauryl sulfate, 2 parts of polyoxyethylene alkyl sulfate, 2 parts of calcium lignin sulfate, 5 parts of white carbon, and 39 parts of kaolin.

Example 3

A granule was produced by crushing and mixing 0.1 parts of the compound of the invention, 1 part of polyoxyethylene nonylphenyl ether, 30 parts of bentonite, and 68.9 parts of talc, and then kneading the mixture with water, followed by granulation and drying.

Example 4

An emulsion was produced by mixing 2 parts of the compound of the invention, 5 parts of Solpol 2680-H (a product of Toho Kagaku Co., Ltd.), 10 parts of methylnaphthalene, and 83 parts of xylene.

Example 5

A liquid formulation was produced by crushing in a wet process 2 parts of the compound of the invention, 2 parts of sodium dioctyl sulfosuccinate, 3 parts of polyoxyethylene-polyoxypropylene copolymer, 4.5 parts of propylene glycol, 1.5 parts of CMC, 2 parts of bentonite, and 86.5 parts of water, until the active ingredient had an average particle size smaller than 5 microns.

Example 6

A liquid formulation was produced by crushing in a wet process 20 parts of the compound of the invention, 3 parts of sodium dioctyl sulfosuccinate, 3 parts of polyoxyethylene-polyoxypropylene copolymer, 4.5 parts of propylene glycol, 0.5 parts of CMC, and 69 parts of water, until the active ingredient had an average particle size smaller than 5 microns.

The compound of the invention and the reference compounds were examined for herbicidal effect and chemical injury in Examples 7 to 9. In the examination, the germination and growth of the test plants were visually observed, and the results were expressed in terms of six grades (0, 1, 2, 3, 4, and 5). Where the test plants grow normally, the sample compound is given the grade of "0" for herbicidal effect or chemical injury, and where the test plants die or do not grow at all, the sample compound is given the grade of "5" for herbicidal effect or chemical injury.

Example 7

Tests on herbicidal effect and chemical injury in wet rice fields wet rice field soil filled in a 150 $cm^2$ plastics pot was sown with seeds of broad-leaved weeds (e.g., Himemisohagi and Konagi) and Hotarui, followed by mixing with a surface layer of about 1 cm deep. Then, tubers of Urikawa and Mizukayatsuri were buried in the surface layer and the pot was flooded. Subsequently, rice seedlings at the two-leaf stage were transplanted. One day after growth in a greenhouse, the wettable powder produced according to Example 2 was applied. A prescribed amount of the wettable powder was diluted with 8 ml of water and the solution was injected into water using a pipet. The test plants were grown in a greenhouse for 19 days and the herbicidal effect and chemical injury were examined. The results are shown in Table 2.

TABLE 2

Herbicidal effect and chemical injury in wet rice field

| Items | Compound of the invention | | Compound A | | Compound B | | Compound C | | Compound D | | Compound E | |
|---|---|---|---|---|---|---|---|---|---|---|---|---|
| Dosage (g/are)* | 1 | 0.3 | 1 | 0.3 | 1 | 0.3 | 1 | 0.3 | 1 | 0.3 | 1 | 0.3 |
| Herbicidal effect | | | | | | | | | | | | |
| Tainubie | 5 | 5 | 0 | 0 | 0 | 0 | 1 | 1 | 5 | 3 | 5 | 3.5 |
| Broad-leaved weeds | 5 | 5 | 0 | 0 | 0 | 0 | 5 | 3 | 5 | 4.5 | 5 | 4.5 |
| Hotarui | 5 | 5 | 0 | 0 | 0 | 0 | 5 | 3 | 4 | 3 | 2 | 1 |
| Urikawa | 5 | 5 | 0 | 0 | 0 | 0 | 0 | 0 | 0 | 0 | 0 | 0 |
| Mizugayatsuri | 5 | 5 | 0 | 0 | 0 | 0 | 0 | 0 | 2 | 0 | 1 | 0 |
| Chemical injury | | | | | | | | | | | | |
| Rice | 1 | 0 | 0 | 0 | 0 | 0 | 1 | 0 | 3 | 0 | 1 | 0 |

*Based on active ingredient.

It is noted from Table 2 that the compound of the invention has a far superior herbicidal effect and chemical injury to that of the comparative compounds A to E when applied to a wet rice field, and is effective against not only Tainubie (major paddy field weed) and broad-leaved weeds but also against Hotarui, Urikawa, and Mizukayatsuri which are strong perennial weeds and difficult to control. This is a surprising effect not predicted by the prior art. The chemical injury to rice was practically negligible.

Example 8

Tests on the herbicidal effect and chemical injury by soil application before germination in upland field Upland field soil filled in a 325 cm² plastics pot was sown with seeds of weed and crop, followed by covering with soil to about 5 mm deep. The wettable powder produced according to Example 2 was applied. A prescribed amount of the wettable powder was diluted with 5 ml of water and the solution was sprayed onto the soil surface using a small spray. The test plants were grown in a greenhouse for 15 days and the herbicidal effect and chemical injury were examined. The results are shown in Table 3. It is noted from Table 3 that the compound of the invention is much more effective against strong upland weeds such as Shiroza (Chenopodiaceae, *Chenopodium album*), Nagabagishigishi (Polygonaceae, *Rumex crispus*), Aobiyu (Amaranthaceae, *Amarunthus viridis*), and Oonamomi (Compositae, *Xanthium canadense*) than the comparative compounds.

TABLE 3

Herbicidal effect and chemical injury by soil application in upland field before germination

| Items | Compound of the invention | | Compound A | | Compound B | | Compound C | | Compound D | | Compound E | |
|---|---|---|---|---|---|---|---|---|---|---|---|---|
| Dosage (g/are)* | 1 | 0.3 | 1 | 0.3 | 1 | 0.3 | 1 | 0.3 | 1 | 0.3 | 1 | 0.3 |
| Herbicidal effect | | | | | | | | | | | | |
| Mehishiba | 4.5 | 3 | 0 | 0 | 0 | 0 | 0 | 0 | 4 | 0 | 4 | 0 |
| Inubiyu | 3 | 0 | 0 | 0 | 0 | 0 | 0 | 0 | 0 | 0 | 0 | 0 |
| Shiroza | 5 | 5 | 0 | 0 | 0 | 0 | 4 | 0 | 4 | 3 | 5 | 0 |
| Nagabagishigishi | 5 | 5 | 0 | 0 | 0 | 0 | 0 | 0 | 4 | 0 | 0 | 0 |
| Aobiyu | 5 | 5 | 0 | 0 | 0 | 0 | 3 | 0 | 3 | 1 | 5 | 0 |
| Oonamomi | 5 | 5 | 0 | 0 | 0 | 0 | 0 | 0 | 2 | 0 | 0 | 0 |
| Chemical injury | | | | | | | | | | | | |
| Corn | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 |

*Based on active ingredient.

Example 9

Tests on herbicidal effect and chemical injury by foliage application in upland field Upland field soil filled in a 325 cm² plastics pot was sown with seeds or weed and crop, followed by covering with soil to about 5 mm deep. The test plants were grown in a greenhouse for 10 days. The wettable powder produced according to Example 2 was applied to the young test plants. A prescribed amount of the wettable powder was diluted with 5 ml of water and the solution was sprayed onto the test plants using a small spray. The test plants were grown in a greenhouse for 20 days and the herbicidal effect and chemical injury were examined. The results are shown in Table 4. It is noted from Table 4 that the compound of the invention is much more effective against Mehishiba (Gramineae, *Digitaria ciliaris*), Inubiyu (Amaranthaceae, *Echinochloa crus-galli*), Hakobe (Caryophyllaceae, *Stellaria media*), Shiroza (Chenopodiaceae, *Chenopodium album*), Nagabagishigishi (Polygonaceae, *Rumex crispus*), Aobiyu (Amaranthaceae, *Amarunthus viridis*), Oonamomi (Compositae, *Xanthium canadense*) and Inugarashi (Cruciferae, *Rorippa indica*), than the comparative compounds A to E.

TABLE 4

Herbicidal effect and chemical injury by foliage application in upland field

| Items | Compound of the invention | | Compound A | | Compound B | | Compound C | | Compound D | | Compound E | |
|---|---|---|---|---|---|---|---|---|---|---|---|---|
| Dosage (g/are)* | 1 | 0.3 | 1 | 0.3 | 1 | 0.3 | 1 | 0.3 | 1 | 0.3 | 1 | 0.3 |
| Herbicidal effect | | | | | | | | | | | | |

TABLE 4-continued

| | Herbicidal effect and chemical injury by foliage application in upland field | | | | | | | | | | | |
|---|---|---|---|---|---|---|---|---|---|---|---|---|
| Items | Compound of the invention | | Compound A | | Compound B | | Compound C | | Compound D | | Compound E | |
| Mehishiba | 5 | 5 | 1 | 1.5 | 0 | 0 | 2.5 | 0 | 4 | 1 | 4 | 0 |
| Inubiyu | 5 | 4.5 | 1.5 | 1.5 | 0 | 0 | 0 | 0 | 4 | 4 | 1 | 1 |
| Hakobe | 5 | 5 | 0 | 0 | 0 | 0 | 0 | 0 | 0 | 0 | 0 | 0 |
| Shiroza | 5 | 5 | 2.5 | 1.5 | 1.5 | 0 | 4.5 | 1.5 | 5 | 5 | 5 | 5 |
| Nagabagishigishi | 5 | 5 | 2 | 1 | 0 | 0 | 3.5 | 1.5 | 5 | 5 | 5 | 5 |
| Aobiyu | 5 | 5 | 0 | 0 | 2 | 0 | 4 | 0 | 3 | 3 | 5 | 3 |
| Oonamomi | 5 | 5 | 0 | 0 | 0 | 0 | 3 | 4.5 | 3.5 | 2 | 2.5 | 2 |
| Inugarashi | 5 | 5 | 0 | 0 | 0 | 0 | 3 | 3.5 | 5 | 4 | 2 | 2 |
| Chemical injury | | | | | | | | | | | | |
| Corn | 4 | 1 | 4 | 1 | 0 | 0 | 0 | 0 | 3 | 3 | 5 | 2 |
| Rice | 1 | 0 | 1 | 1 | 0 | 0 | 0 | 0 | 2 | 2 | 1 | 0 |
| Wheat | 2 | 0 | 2 | 1 | 0 | 0 | 0 | 0 | 2 | 1 | 1 | 1 |

*Based on active ingredient.

We claim:

1. A compound 5-t-butyl-3-(4-chloro-2-fluoro-5-propargyloxy-phenyl)-1,3,4-oxadiazol-2-one.

2. A herbicidal composition, comprising a herbicidally effective amount of the compound 5-t-butyl-3-(4-chloro-2-fluoro-5-propargyl-oxy-phenyl)-1,3,4-oxadiazole-2-one, and at least one carrier.

3. The herbicidal composition of claim 2, wherein said composition further includes a surface active agent.

4. The herbicidal composition of claim 2, wherein said compound comprises from about 0.05 to about 80% by weight of said composition.

5. A herbicidal composition as claimed in claim 2, wherein said carrier is solid and comprises clay, kaolin clay, talc, diatomaceous earth, bentonite, acid clay, calcium carbonate or vegetable powder.

6. A herbicidal composition as claimed in claim 2, wherein said carrier is liquid and comprises toluene, xylene, methyl naphthalene, butanol, isopropanol, ethylene glycol, cyclohexanone, methyl ethyl ketone, animal oils or vegetable oils.

* * * * *